United States Patent
Huntsman et al.

(10) Patent No.: US 11,723,790 B2
(45) Date of Patent: Aug. 15, 2023

(54) VIBRATIONAL ORAL APPLIANCE WITH MANDIBULAR ADVANCEMENTS

(71) Applicant: Vivos Therapeutics, Inc., Highlands Ranch, CO (US)

(72) Inventors: Todd Nickolas Huntsman, Flower Mound, TX (US); Braden Charles Bennett, Provo, UT (US); Justin Dean Harris, Lehi, UT (US); Cathryn H. Bonar, Owensboro, KY (US)

(73) Assignee: VIVOS THERAPEUTICS, INC., Highlands Ranch, CO (US)

( * ) Notice: Subject to any disclaimer, the term of this patent is extended or adjusted under 35 U.S.C. 154(b) by 81 days.

(21) Appl. No.: 17/522,769

(22) Filed: Nov. 9, 2021

(65) Prior Publication Data
US 2023/0142812 A1    May 11, 2023

(51) Int. Cl.
*A61F 5/56* (2006.01)
*A61C 7/36* (2006.01)
(Continued)

(52) U.S. Cl.
CPC .............. *A61F 5/566* (2013.01); *A61C 7/008* (2013.01); *A61C 7/08* (2013.01); *A61C 7/10* (2013.01); *A61C 7/36* (2013.01)

(58) Field of Classification Search
CPC ...... A61F 5/56; A61F 5/566; A61F 2005/563; A61C 7/002; A61C 7/008; A61C 7/10; A61C 7/08; A61C 7/36
See application file for complete search history.

(56) References Cited

U.S. PATENT DOCUMENTS

| 3,898,736 A | 8/1975 | Bergersen |
| 3,939,598 A | 2/1976 | Bergersen |

(Continued)

FOREIGN PATENT DOCUMENTS

| CA | 2027707 A1 | 4/1992 |
| CA | 2675496 C | 6/2012 |

(Continued)

OTHER PUBLICATIONS

Apex, "Dental Sleep Lab, Kava Dorsal, Kava Herbst", downloaded from the internet Aug. 9, 2021, pp. 1 through 38, Apex Dental Sleep Lab, https://apexsleep.com.

(Continued)

*Primary Examiner* — Camtu T Nguyen
(74) *Attorney, Agent, or Firm* — Armstrong Teasdale LLP (57) ABSTRACT

Described herein is an oral appliance. The oral appliance includes upper and lower trays that each include at least one axial spring configured to contact a palatal/lingual surface of at least one tooth, where each axial spring is coupled to the respective upper or lower tray, and where each axial spring is configured to produce and transmit intermittent, cyclic forces to the palatal/lingual surface of the tooth to promote palatal and upper/lower jaw development. The upper and lower trays each include an expansion mechanism to enable adjustment of the size of the upper and lower trays to account for palatal expansion and upper and lower jaw development. The oral appliance includes first and second adjustable hinge arms that are removably connected to the upper and lower trays so that the oral appliance advances the mandible to provide temporary relief from sleep disordered breathing, sleep apnea and/or snoring.

22 Claims, 7 Drawing Sheets

(51) Int. Cl.
*A61C 7/00* (2006.01)
*A61C 7/08* (2006.01)
*A61C 7/10* (2006.01)

(56) References Cited

U.S. PATENT DOCUMENTS

| | | |
|---|---|---|
| 3,950,851 A | 4/1976 | Bergersen |
| 3,967,379 A | 7/1976 | Bergersen |
| 4,025,893 A | 5/1977 | Bergersen |
| 4,073,061 A | 2/1978 | Bergersen |
| 4,092,626 A | 5/1978 | Bergersen |
| 4,139,944 A | 2/1979 | Bergersen |
| 4,330,272 A | 5/1982 | Bergersen |
| 4,354,886 A | 10/1982 | Bergersen |
| 4,363,947 A | 12/1982 | Bergersen |
| 4,501,956 A | 2/1985 | Bergersen et al. |
| 4,650,960 A | 3/1987 | Bergersen |
| 4,665,302 A | 5/1987 | Bergersen |
| 4,764,112 A | 8/1988 | Bergersen |
| 4,784,605 A | 11/1988 | Bergersen |
| 4,797,093 A | 1/1989 | Bergersen |
| 4,799,884 A | 1/1989 | Bergersen |
| 4,830,612 A | 5/1989 | Bergersen |
| 4,856,992 A | 8/1989 | Bergersen |
| 4,881,896 A | 11/1989 | Bergersen |
| 4,898,535 A | 2/1990 | Bergersen |
| 4,919,612 A | 4/1990 | Bergersen |
| 4,979,925 A | 12/1990 | Bergersen |
| 4,986,751 A | 1/1991 | Bergersen |
| 5,002,485 A * | 3/1991 | Aagesen .......... A61C 7/00 433/7 |
| 5,037,294 A | 8/1991 | Bergersen |
| 5,037,295 A | 8/1991 | Bergersen |
| D322,674 S | 12/1991 | Bergersen |
| D323,215 S | 1/1992 | Bergersen |
| 5,194,004 A | 3/1993 | Bergersen |
| 5,203,695 A | 4/1993 | Bergersen |
| D355,311 S | 2/1995 | Bergersen |
| 5,500,964 A | 3/1996 | Bergersen |
| 5,505,118 A | 4/1996 | Amesen et al. |
| D376,161 S | 12/1996 | Bergersen |
| 5,634,484 A | 6/1997 | Vodila et al. |
| 5,645,420 A | 7/1997 | Bergersen |
| 5,675,739 A | 10/1997 | Eilert et al. |
| 5,876,199 A | 3/1999 | Bergersen |
| 5,882,192 A | 3/1999 | Bergersen |
| 5,925,102 A | 7/1999 | Eilert et al. |
| 5,948,065 A | 9/1999 | Eilert et al. |
| 6,129,084 A | 10/2000 | Bergersen |
| D436,527 S | 1/2001 | Bergersen |
| D436,528 S | 1/2001 | Bergersen |
| D436,529 S | 1/2001 | Bergersen |
| 6,282,560 B1 | 8/2001 | Eilert et al. |
| 6,582,225 B1 | 6/2003 | Bergersen |
| 6,591,262 B1 | 7/2003 | MacLellan et al. |
| 6,626,664 B1 | 9/2003 | Bergersen |
| 6,648,639 B2 | 11/2003 | Mao |
| 6,654,780 B1 | 11/2003 | Eilert et al. |
| 6,823,346 B2 | 11/2004 | MacLellan et al. |
| 6,832,912 B2 | 12/2004 | Mao |
| 7,029,276 B2 | 4/2006 | Mao |
| 7,089,294 B1 | 8/2006 | Baskey et al. |
| 7,234,933 B2 | 6/2007 | Bergersen |
| 7,294,141 B2 | 11/2007 | Bergersen |
| 7,458,810 B2 | 12/2008 | Bergersen |
| 7,493,380 B2 | 2/2009 | Aman et al. |
| 7,532,583 B2 | 5/2009 | Bivens et al. |
| 7,536,375 B2 | 5/2009 | Schisler et al. |
| D600,350 S | 9/2009 | Singh |
| 7,716,062 B2 | 5/2010 | Bergersen |
| 7,725,420 B2 | 5/2010 | Schisler et al. |
| 7,810,502 B1 | 10/2010 | Nguyen et al. |
| 7,817,578 B2 | 10/2010 | Bivens et al. |
| 7,861,721 B2 | 1/2011 | Bergersen |
| 7,887,324 B2 * | 2/2011 | Singh .......... A61C 7/10 433/7 |
| D636,083 S | 4/2011 | Singh |
| 7,963,765 B2 | 6/2011 | Bergersen |
| 7,975,701 B2 | 7/2011 | Bergersen |
| 8,133,050 B2 | 3/2012 | Bergersen |
| 8,192,196 B2 * | 6/2012 | Singh .......... A61F 5/566 433/7 |
| 8,303,301 B2 | 11/2012 | Bergersen |
| D704,843 S | 5/2014 | Singh |
| D713,530 S | 9/2014 | Singh |
| 8,870,566 B2 | 10/2014 | Bergersen |
| 8,939,762 B2 | 1/2015 | Lowe |
| D722,170 S | 2/2015 | Bergersen |
| D722,171 S | 2/2015 | Bergersen |
| 9,028,250 B2 | 5/2015 | Spaulding et al. |
| D731,659 S | 6/2015 | Singh |
| D736,945 S | 8/2015 | Singh |
| D739,029 S | 9/2015 | Bergersen |
| 9,130,744 B1 | 9/2015 | King et al. |
| D759,252 S | 6/2016 | Bergersen |
| 9,370,405 B2 | 6/2016 | Lowe |
| 9,393,083 B2 | 7/2016 | Bergersen |
| 9,498,373 B2 | 11/2016 | Scheffel |
| 9,517,113 B2 | 12/2016 | Bergersen |
| 9,662,184 B2 | 5/2017 | Lowe |
| 9,668,828 B2 | 6/2017 | Lowe et al. |
| 9,675,305 B2 | 6/2017 | Bergersen |
| 9,700,384 B2 | 7/2017 | Lowe |
| 9,949,867 B2 * | 4/2018 | Veis .......... A61C 7/08 |
| 9,993,317 B2 * | 6/2018 | Kottemann .......... A61C 7/36 |
| 10,524,742 B2 | 1/2020 | Bergersen |
| 10,537,407 B2 | 1/2020 | Bergersen |
| 10,583,031 B2 * | 3/2020 | Quaka .......... A61F 5/566 |
| 10,583,032 B2 | 3/2020 | Rogers |
| 10,588,776 B2 | 3/2020 | Cam et al. |
| 10,772,756 B2 | 9/2020 | Vaska et al. |
| 10,874,593 B2 | 12/2020 | Bergersen |
| 2003/0138752 A1 | 7/2003 | Bergersen |
| 2003/0224312 A1 | 12/2003 | Bergersen |
| 2003/0224313 A1 | 12/2003 | Bergersen |
| 2003/0224314 A1 | 12/2003 | Bergersen |
| 2003/0225594 A1 | 12/2003 | Bergersen |
| 2004/0058295 A1 | 3/2004 | Bergersen |
| 2004/0059382 A1 | 3/2004 | Bergersen |
| 2004/0152032 A1 | 8/2004 | Bergersen |
| 2005/0037311 A1 | 2/2005 | Bergersen |
| 2006/0099546 A1 | 5/2006 | Bergersen |
| 2007/0051643 A1 | 3/2007 | Bergersen |
| 2007/0240724 A1 | 10/2007 | Bergersen |
| 2007/0264605 A1 * | 11/2007 | Belfor .......... A61C 7/00 433/6 |
| 2008/0236597 A1 | 10/2008 | Bergersen |
| 2010/0151402 A1 * | 6/2010 | Williams .......... A61C 7/282 433/7 |
| 2011/0287377 A1 * | 11/2011 | Hang .......... A61C 7/00 433/7 |
| 2013/0323668 A1 * | 12/2013 | Ash .......... A61C 7/36 433/19 |
| 2015/0169845 A1 | 6/2015 | Bradley |
| 2017/0325913 A1 | 11/2017 | Bergersen |
| 2020/0345534 A1 * | 11/2020 | Lucas .......... A61B 5/682 |

FOREIGN PATENT DOCUMENTS

| | | |
|---|---|---|
| CA | 2688688 C | 1/2014 |
| CN | 102596091 A | 7/2012 |
| EP | 2376015 B1 | 5/2019 |
| GB | 1176048 A | 1/1970 |
| JP | H0326248 A | 2/1991 |
| JP | H03234254 A | 10/1991 |
| JP | H04183462 A | 6/1992 |
| KR | 101688545 B1 | 12/2016 |
| MX | 2009010146 A | 10/2009 |
| MX | 2014011068 A | 3/2015 |
| MY | 130245 A | 6/2007 |
| TW | 200806260 A | 2/2008 |
| WO | 2004064662 A2 | 8/2004 |

(56) References Cited

FOREIGN PATENT DOCUMENTS

| | | | |
|---|---|---|---|
| WO | 2004064662 | A3 | 8/2004 |
| WO | 2007030543 | A2 | 3/2007 |
| WO | 2007030543 | A3 | 3/2007 |
| WO | WO 2019/046717 | A1 * | 3/2019 |
| YU | 31300 | A | 10/2002 |
| YU | 49365 | B | 9/2005 |
| YU | 103104 | A | 5/2006 |
| YU | 103904 | A | 5/2006 |

OTHER PUBLICATIONS

Somnomed, "SomnoDent Flex", downloaded from the internet Aug. 9, 2021, pp. 1 through 3, https://somnomed.com/en/dentists/somnodent/somnodent-flex/.

Somnomed, "SomnoDent Fusion", SomnoMed Product Range, downloaded from the internet Aug. 9, 2021, pp. 1 through 6, https://somnomed.com/en/dentists/somnodent/somnodent-fusion/.

* cited by examiner

VIBRATIONAL ORAL APPLIANCE WITH MANDIBULAR ADVANCEMENTS

FIELD OF DISCLOSURE

The present disclosure is directed to an oral appliance. The oral appliance advances the mandible to provide temporary relief from sleep disordered breathing, sleep apnea and/or snoring.

BACKGROUND

Sleep apnea is a serious, chronic disease that adversely impacts millions of people. Over the years, many treatments and devices have been developed to help patients deal with the symptoms of sleep apnea. In addition, some researchers have devoted time and energy to finding ways to attack the root cause of the disease. For example, U.S. Pat. No. 7,887,324 describes a protocol for correcting common orthodontic and craniofacial abnormalities that lead to sleep apnea and other breathing disorders. The protocol of U.S. Pat. No. 7,887,324 uses a vibrational orthopedic-orthodontic appliance that induces craniofacial homeostasis by triggering a patient's genome. This treatment protocol changes the shape of the airway and upper and lower jaws of the patient. As a result of the treatment, a patient's breathing disorder could be significantly reduced in a life-changing way.

However, this protocol to correct the airway and jaw of the patient takes some time. During treatment, the patient still suffers from a breathing disorder and needs short term relief. Many devices for short term relief are available on the market, including devices that force the advancement of the mandible during sleep. Yet because the appliance of U.S. Pat. No. 7,887,324 is worn at night, its use conflicts with using other devices for short-term relief while sleeping. Moreover, adaptations of the appliance of U.S. Pat. No. 7,887,324 to provide short term relief have drawbacks.

Therefore, there is a need in the art for an improved device that provides short term relief from breathing disorders and also addresses the root cause of the disease.

The present disclosure provides an oral appliance that provides short term relief from breathing disorders and also addresses the root cause of the disease. In particular, the oral appliance advances the mandible to provide temporary relief from sleep disordered breathing, sleep apnea and/or snoring.

BRIEF DESCRIPTION OF THE DISCLOSURE

In one aspect, provided herein is an oral appliance comprising:

an upper tray configured to be positioned over an upper dental arch of a patient, the upper tray including first and second posts located bilaterally on a buccal side of a posterior of the upper tray wherein the first post extends from the right-side of the upper tray and the second post extends from the left-side of the upper tray;

a lower tray configured to be positioned over a lower dental arch of the patient, the lower tray including third and fourth posts located bilaterally on a labial side of an anterior of the lower tray wherein the third post extends from the right-side of the lower tray and the fourth post extends from the left-side of the lower tray; and a first adjustable hinge arm and a second adjustable hinge arm, wherein the first adjustable hinge arm is removably coupled between the first and third posts and the second adjustable hinge arm is removably coupled between the second and fourth posts, wherein the first adjustable hinge arm and the second adjustable hinge arm are each individually configured to be held in place by O-rings and, when held in place, interlock the upper tray and the lower tray together to produce a desired amount of mandibular advancement;

wherein the upper and lower trays are each individually coupled to at least one axial spring configured to contact a palatal/lingual surface of at least one tooth, wherein the at least one axial spring of the upper tray and the at least one axial spring of the lower tray are each individually configured to produce and transmit intermittent, cyclic forces to the palatal/lingual surface of the at least one tooth; and wherein the upper and lower trays each individually comprise at least two sections coupled by an expansion mechanism to enable adjustment of the size of the upper and lower trays to account for palatal expansion and upper and lower jaw development.

In another aspect, provided herein is an oral appliance comprising:

an upper tray configured to be positioned over an upper dental arch of a patient, the upper tray including first and second posts located bilaterally on a buccal side of a posterior of the upper tray wherein the first post extends from the right-side of the upper tray and the second post extends from the left-side of the upper tray;

wherein the first post is configured to receive a first adjustable hinge arm and the second post is configured to receive a second adjustable hinge arm, wherein the first and second adjustable hinge arms are optionally non-permanently attached to the first and second posts, respectively, with O-rings;

wherein the upper tray comprises at least one axial spring configured to contact a palatal/lingual surface of at least one tooth, wherein the at least one axial spring is coupled to the upper tray, wherein the at least one axial spring is configured to produce and transmit intermittent, cyclic forces to the palatal/lingual surface of the tooth; and wherein the upper tray comprises at least two sections coupled by an expansion mechanism to enable adjustment of the size of the upper tray to account for palatal expansion and upper jaw development.

BRIEF DESCRIPTION OF THE DRAWINGS

Embodiments of the present invention can be more easily understood and further advantages and uses thereof more readily apparent, when considered in view of the description of the various embodiments and the following figures in which.

DETAILED DESCRIPTION

In the following detailed description, reference is made to the accompanying drawings that form a part hereof, and in which is shown by way of specific illustrative embodiments in which the invention may be practiced. These embodiments are described in sufficient detail to enable those skilled in the art to practice the invention, and it is to be understood that other embodiments may be utilized and that logical, mechanical and electrical changes may be made without departing from the scope of the present invention. The following detailed description is, therefore, not to be taken in a limiting sense.

Oral Appliance: Overview

Oral appliances in accordance with the present disclosure provide short term relief from breathing disorders and also address the root cause of the disease. Generally, the oral appliances advance the mandible to provide temporary relief from sleep disordered breathing, sleep apnea and/or snoring.

Figure 1A:
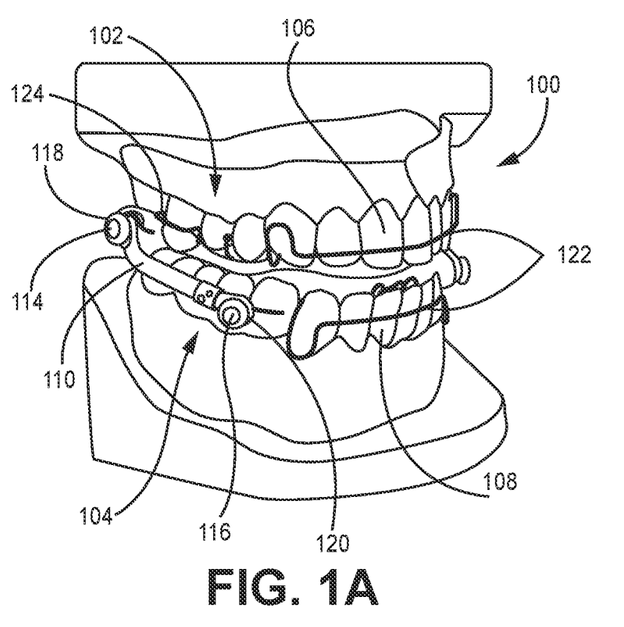
FIG. 1A is a perspective view of an oral appliance shown positioned on a set of teeth according to one embodiment of the present invention.

FIG. 1A depicts a perspective view of one embodiment of a vibrational oral appliance with mandibular advancement, indicated generally at 100, and constructed according to the present invention. Oral appliance 100 is designed to perform at least two functions. First, oral appliance 100 uses vibrational elements (such as 3-D axial springs, as described in more detail below) to promote palatal and upper/lower jaw development. This function makes physical changes to the patient for long-term correction of breathing disorders. Second, oral appliance 100 is configured to be used as a sleep aide to provide immediate relief for patients suffering from sleep-disordered breathing, including, but not limited to, obstructive sleep apnea (OSA) and snoring. To accomplish this, oral appliance 100 includes a mechanism for mandibular advancement. In some embodiments, this mechanism is a removable part that, when inserted, controls the relative position of the upper and lower jaws of the patient (referred to as mandibular advancement). Thus, the same oral appliance performs two functions: (1) it promotes palatal and upper/lower jaw development, and (2) it provides mandibular advancement for temporary relief from symptoms of sleep-disordered breathing and/or sleep apnea.

In some embodiments, the mechanism for mandibular advancement is used only during sleep. In some embodiments, the mechanism for mandibular advancement is removed from the oral appliance, and the oral appliance continues to perform the first function to promote palatal and upper/lower jaw development.

In some embodiments, oral appliance 100 includes an upper tray 102 and a lower tray 104. Generally, upper tray 102 is configured to be positioned over an upper dental arch 106. Generally, lower tray 104 is configured to be positioned over a lower dental arch 108.

In some embodiments, oral appliance 100 comprises one hinge arm, two hinge arms, three hinge arms, four hinge arms, or more than four hinge arms. In some embodiments, oral appliance 100 comprises removable hinge arms 110 located on opposite sides of oral appliance 100. Only one hinge arm is fully visible in FIG. 1A because of the perspective view. In some embodiments, oral appliance 100 comprises removable hinge arms 110 that interlock upper tray 102 and lower tray 104 when installed.

In some embodiments, the length of hinge arm 110 is adjustable. In some embodiments, the length of hinge arm 110 is set for a patient so that the lower jaw (mandible) of the patient is advanced to an appropriate position to open the airway to provide temporary relief from obstructive sleep apnea (OSA), snoring, and/or other sleep disordered breathing.

Generally, hinge arm 110 may be selected from any suitable hinge arm or interlocking mechanism known in the art. In some embodiments, hinge arm 110 is a Herbst-style arm or appliance that has an adjustable length. The specific interlocking arm shown in FIGS. 1A and 1B is shown by way of example and not by way of limitation.

In some embodiments, oral appliance 100 comprises one post, two posts, three posts, four posts, or more than four posts. In some embodiments, oral appliance 100 comprises at least one hinge arm 110 coupled between at least two posts.

Figure 1B:
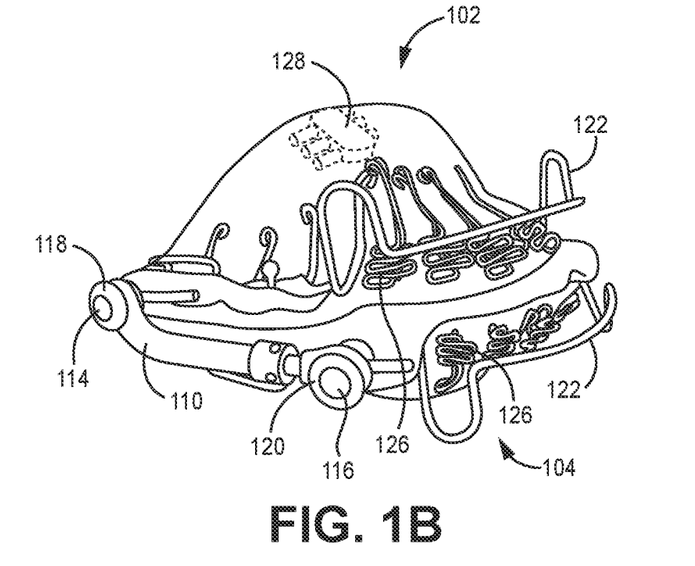
FIG. 1B is a perspective view of the oral appliance of FIG. 1A.

In the example shown in FIGS. 1A and 1B, hinge arm 110 is coupled between two posts, post 114 and post 116. Post 114 is positioned on the buccal side of the posterior of upper tray 102 such that post 114 extends from the left-side of the upper tray 102. In some embodiments, a second post 114 on the other side of the jaw (not visible in FIGS. 1A and 1B, but shown in FIG. 2) extends from a similar position on the right-side of upper tray 102. In some embodiments, post 116 is positioned on the labial side of the anterior of lower tray 104 such that post 116 extends from the left-side of the lower tray. In some embodiments, a second post 116 (not visible in FIGS. 1A and 1B, but shown in FIGS. 4 and 5A) extends from a similar position on the right-side of the lower tray 104. Generally, when the hinge arm 110 is attached to the upper and lower trays 102 and 104, hinge arm 110 is held in place by an attachment mechanism selected from any suitable attachment mechanism known in the art. In some embodiments, when the hinge arm 110 is attached to the upper and lower trays 102 and 104, hinge arm 110 is held in place by one or more O-rings. In some embodiments, such as the embodiments shown in FIGS. 1A and 1B, when the hinge arm 110 is attached to the upper and lower trays 102 and 104, hinge arm 110 is held in place by O-rings 118 and 120, respectively.

Generally, upper tray 102 and lower tray 104 are held in place with any suitable means known in the art. In some embodiments, upper tray 102 and lower tray 104 are held in place with labial bows 122. In some embodiments, labial bow 122 is formed of an arch wire that wraps around the front of the teeth. In some embodiments, upper tray 102 and lower tray 104 are held in place with clasps 124. In some embodiments, upper tray 102 and lower tray 104 are held in place with labial bows 122 and clasps 124.

Figure 6A:
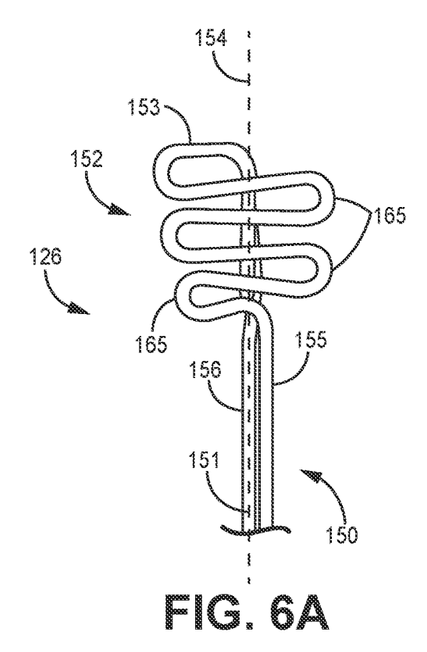
FIG. 6A is a front view of a three dimensional (3-D) axial spring according to one embodiment of the present invention.
Figure 6B:
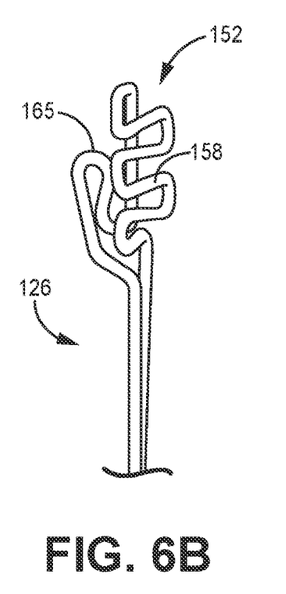
FIG. 6B is a perspective view of a three dimensional (3-D) axial spring according to one embodiment of the present invention.
Figure 6C:
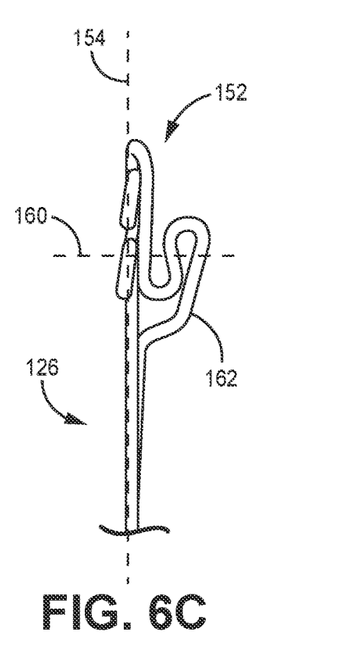
FIG. 6C is a side view of a three dimensional (3-D) axial spring according to one embodiment of the present invention.

In some embodiments, oral appliance 100 uses three-dimensional (3-D) axial springs 126 and an expansion mechanism 128 to promote correction to the airway and upper and lower jaw of the patient using the techniques described in U.S. Pat. No. 7,887,324. U.S. Pat. No. 7,887,324 is incorporated herein by reference. One example of an expansion mechanism 128 is shown in FIG. 3B. One embodiment of 3-D axial springs is described below and is shown in FIGS. 6A-6C.

Upper Tray of Oral Appliance

Figure 2:
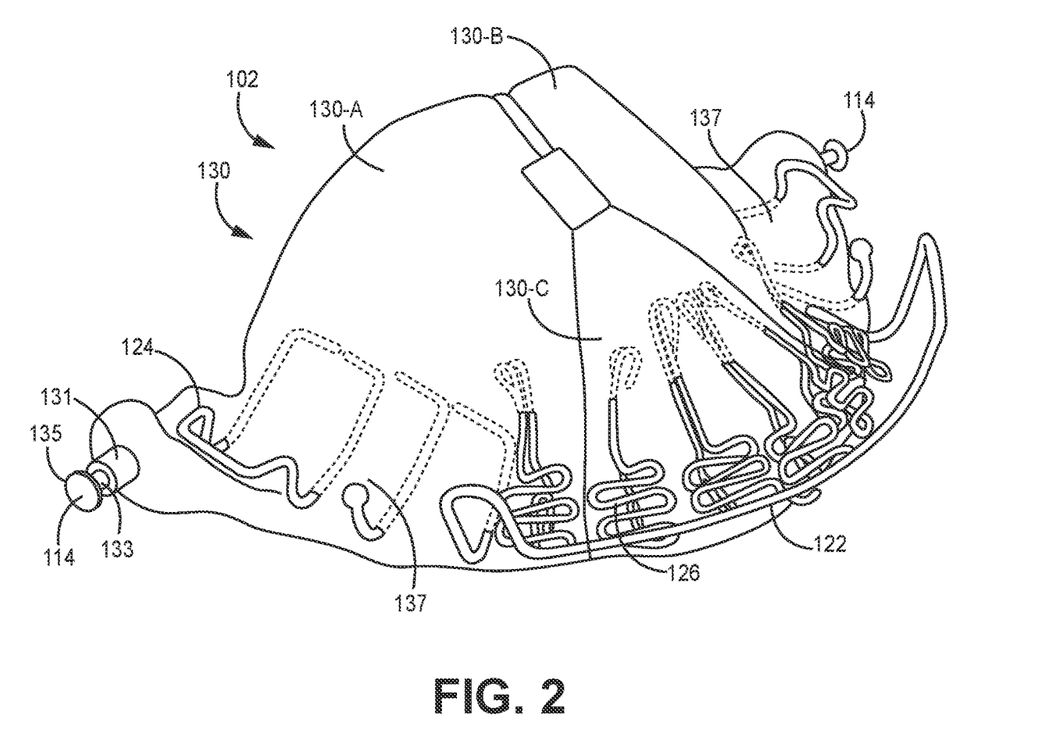
FIG. 2 is a perspective view of one embodiment of an upper tray of the oral appliance of FIG. 1.

As shown in FIG. 2, upper tray 102 includes base plate 130. Generally, base plate 130 is formed of any suitable material for manufacture of oral applications known in the art. In some embodiments, base plate 130 is formed of a hard acrylic material.

In some embodiments, base plate 130 is formed from one part, two parts, three parts, or more than three parts. In some embodiments, the part(s) of base plate 130 are adjustable with an expansion mechanism. Generally, the expansion mechanism may be selected from any suitable expansion mechanism known in the art. In some embodiments, the expansion mechanism is configured to enable upper tray 102 to change in size to accommodate growth and changes in the upper dental arch/palate of the patient. In some embodiments, the expansion mechanism is selected from jackscrews, wires, wires bent with omega-shaped loops, and combinations thereof.

In some embodiments, the part(s) of base plate 130 are adjustable with at least one jackscrew. In some embodiments, the part(s) of base plate 130 are adjustable with at least two jackscrews.

Figure 3A:
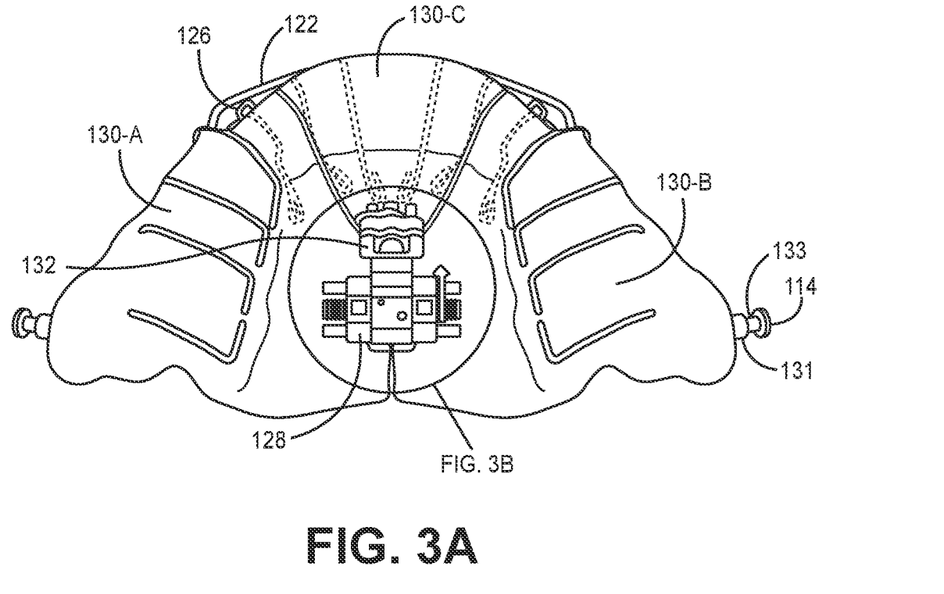
FIG. 3A is a bottom view of the upper tray of FIG. 2.
Figure 3B:
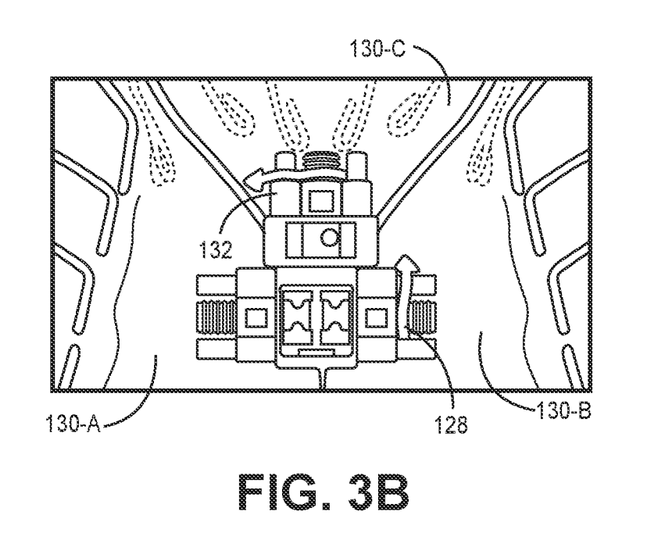
FIG. 3B is a close-up view of a palatal expansion system of the upper tray of FIG. 2.

In the embodiments shown in FIG. 2 and FIGS. 3A-3B, base plate 130 is formed in three parts, namely left part 130-A, right part 130-B and center part 130-C. As shown in FIG. 3A, left part 130-A and right part 130-B of base plate 130 are connected by an intervening midline jackscrew 128 that enables upper tray 102 to expand to account for palatal growth due to the use of 3-D axial springs 126. Additionally, in this embodiment, upper tray 102 also includes jackscrew 132 that couples center part 130-C to the rest of base plate 130 to account for changes in the front of the patient's upper dental arch. By adjusting jackscrew 132, center part 130-C of base plate 130 moves anteriorly and posteriorly to fit upper tray 102 to the patient's dental arch. Similarly, by adjusting jackscrew 128, left and right parts 130-A and 130-B move away from or toward the centerline of the dental arch to further fit the upper tray to the dental arch of the patient. The expansion mechanisms illustrated by jackscrews 128 and 132 are shown by way of example and not by way of limitation.

In some embodiments, such as the embodiment shown in FIG. 3A, base plate 130 also includes extensions or overlays 137 of the plate body that symmetrically overlay the biting (occlusal) surfaces of at least two of the patient's teeth in the space where those teeth would normally contact the opposing teeth from the lower jaw. The thickness of the occlusal coverage ranges from approximately 0.5 mm to approximately 5.0 mm, as determined by orthodontic equilibration, and may be absent in certain locations or spots, if required. The base plate body itself has a thickness that varies, and ranges from about 1.0 mm to about 5.0 mm, depending upon the components embedded within it.

Figure 3C:
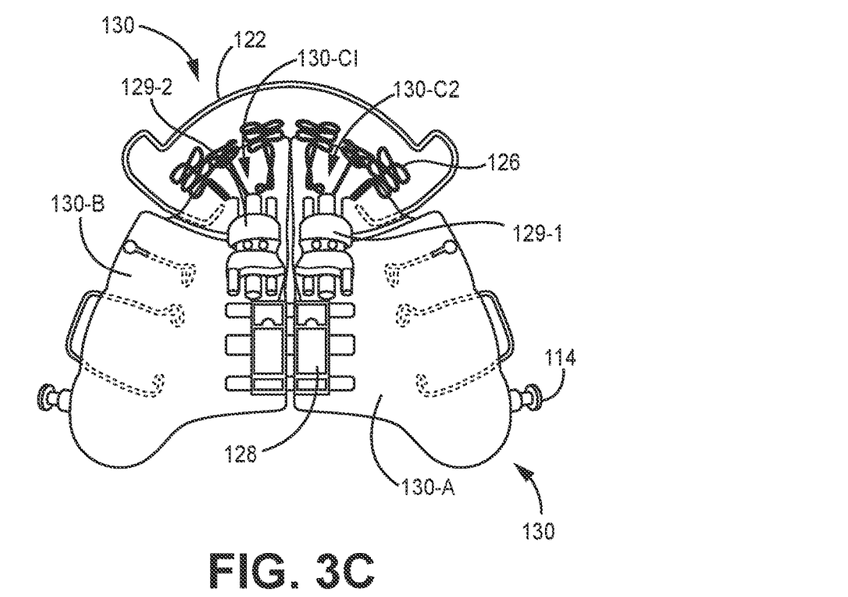
FIG. 3C is a bottom view of an upper tray of the oral appliance of FIG. 1 with a first palatal expansion system according to one embodiment of the present invention.
Figure 3D:
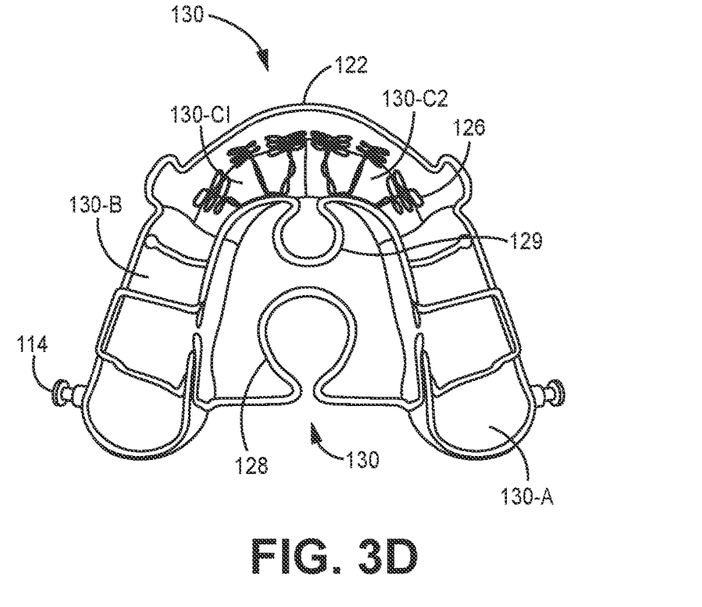
FIG. 3D is a bottom view of an upper tray of the oral appliance of FIG. 1 with a second palatal expansion system according to one embodiment of the present invention.

In some embodiments, the base plate 130 of upper tray 102 is configured in other ways to accommodate changes in the palate and upper and lower jaw. In some embodiments, the base plate 130 includes one portion, two portions, three portions, or more than three portions. In some embodiments, the base plate 130 is divided into four portions such as shown, for example, in FIG. 3C and FIG. 3D. In the embodiment shown in FIG. 3C, the posterior of base plate 130 is divided into two halves: first portion 130-A and second portion 130-B. First half 130-A and second half 130-B are interconnected by an intervening jackscrew assembly 128. Additionally, the anterior portion of base plate 130 is also divided into two halves: third portion 130-C1 and fourth portion 130-C2. Third portion 130-C1 is interconnected with second portion 130-B by intervening jackscrew assembly 129-2. Fourth portion 130-C2 is interconnected with first portion 130-A by intervening jackscrew assembly 129-1. In yet another embodiment, shown in FIG. 3D, base plate 130 includes first and second portions 130-A and 130-B that are interconnected by an expansion mechanism 128. In this embodiment, expansion mechanism 128 is a wire bent with an omega-shaped loop to allow expansion of the upper tray 102. Additionally, base plate 130 also includes third and fourth portions 130-C1 and 130-C2 that are interconnected by expansion mechanism 129. In this embodiment, expansion mechanism 129 is a wire bent with an omega-shaped loop to allow for further expansion of upper tray 102.

In some embodiments, for example as shown in FIG. 1A, the upper tray 102 also includes at least one post 114 that controls mandibular advancement for oral appliance 100. In some embodiments, post 114 enables interlocking of upper tray 102 with lower tray 104 through one or more removable, adjustable hinge arms 110. In some embodiments, such as the embodiment shown in FIG. 2, post 114 includes a cylindrical body 131 that is embedded in the side of base plate 130. Adjacent to the base plate 130, cylindrical body of post 114 has a first diameter. At an end of post 114 opposite the base plate 130, post 114 includes an end cap 135 and a segment 133 of post 114 that includes a second, reduced diameter compared to the first diameter of cylindrical body 131 adjacent to the base plate 130. The end cap 135 and the segment of reduced diameter 133 provide a mechanism for O-ring 118 to hold adjustable hinge arm 110 in place on upper tray 102, as shown in FIGS. 1A, 1B, and 2).

Lower Tray of Oral Appliance

Figure 4:
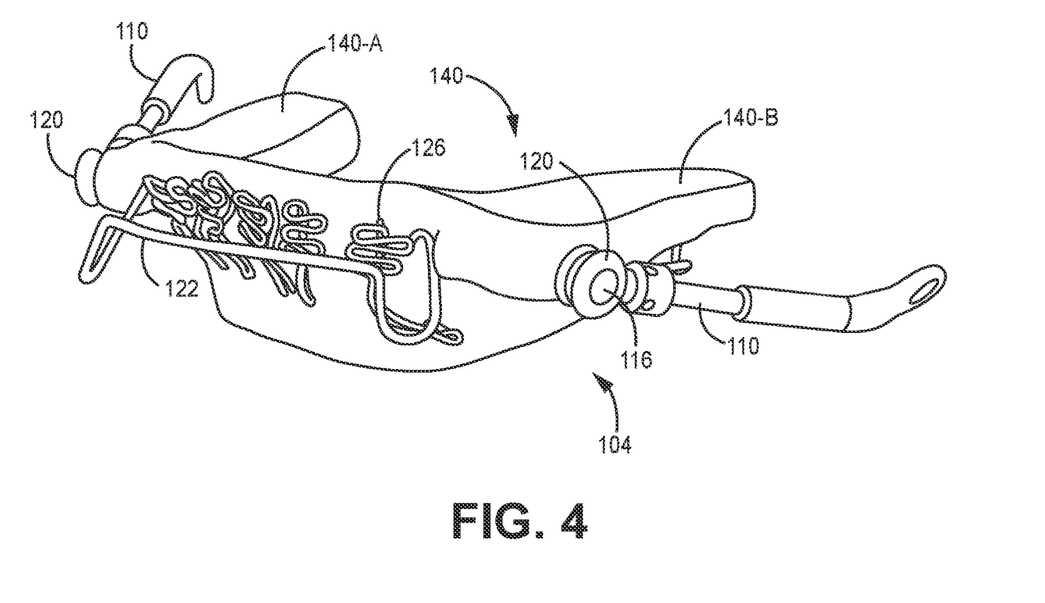
FIG. 4 is a perspective view of one embodiment of a lower tray of the oral appliance of FIG. 1.

FIG. 4 is a perspective view of one embodiment of the lower tray 104 of oral appliance 100. Lower tray 104 comprises adjustable hinge arms 110 attached to posts 116. Lower tray 104 includes base plate 140.

Generally, base plate 140 is formed of any suitable material for manufacture of oral applications known in the art. In some embodiments, base plate 140 is formed of a hard acrylic material.

In some embodiments, base plate 140 is formed from one part, two parts, three parts, or more than three parts. In some embodiments, the part(s) of base plate 140 are adjustable with an expansion mechanism. Generally, the expansion mechanism may be selected from any suitable expansion mechanism known in the art. In some embodiments, the expansion mechanism is selected from jackscrews, wires, wires bent with omega-shaped loops, and combinations thereof.

Figure 5A:
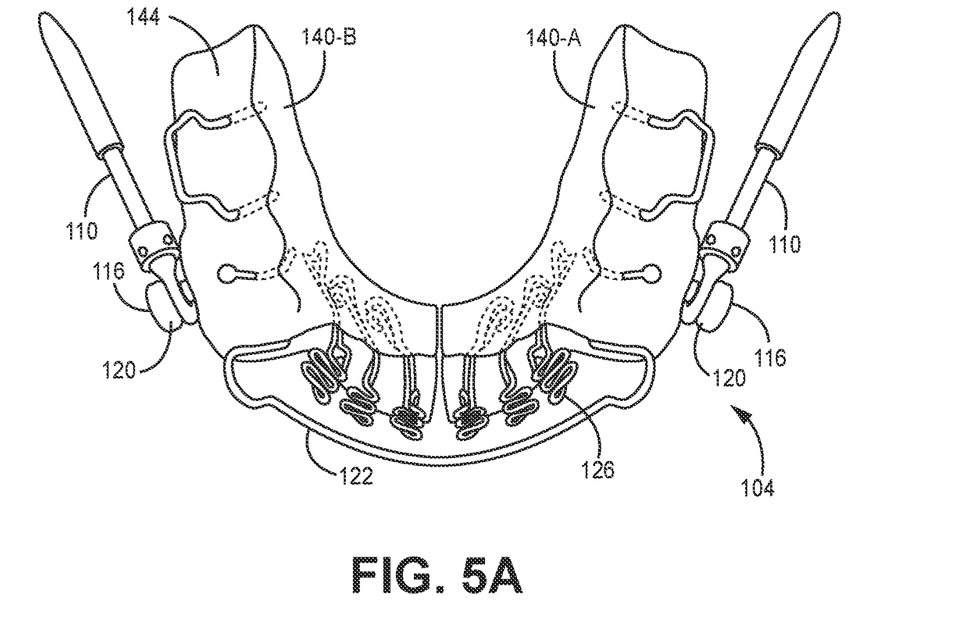
FIG. 5A is a bottom view of the lower tray of FIG. 4.
Figure 5B:
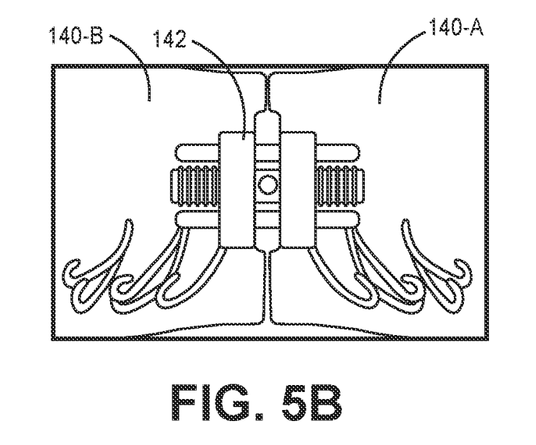
FIG. 5B is a close-up view of a palatal expansion system of the lower tray of FIG. 4.

In the embodiment of FIG. 4, base plate 140 is formed in two parts, namely left part 140-A, and right part 140-B. As shown in FIGS. 5A and 5B, left part 140-A and right part 140-B of base plate 140 are connected by an intervening midline jackscrew 142 that enables lower tray 104 to expand to account for palatal growth due to the use of 3-D axial springs 126. By adjusting jackscrew 142, left and right parts 140-A and 140-B move away from or toward the centerline of the dental arch to fit the lower tray to the dental arch of the patient.

In some embodiments, for example as shown in FIGS. 5A and 5B, base plate 140 includes extensions or overlays 144 of the plate body that symmetrically overlay the biting (occlusal) surfaces of at least two of the patient's teeth in the space where those teeth would normally contact the opposing teeth from the upper jaw. The thickness of the occlusal coverage ranges from approximately 0.5 mm to approximately 5.0 mm, as determined by orthodontic equilibration, and may be absent in certain locations or spots, if required. The base plate body itself has a thickness that varies, and ranges from about 1.0 mm to about 5.0 mm, depending upon the components embedded within it.

In some embodiments, posts 116 of lower tray 104 have a structure that is similar to posts 114 of upper tray 102.

Three-Dimensional (3-D) Axial Springs

In some embodiments, the upper tray 102 and the lower tray 104 each individually comprise at least one spring. Generally, the spring is selected from any suitable spring known in the art to provide cyclic intermittent signaling that stimulates a patient's genome during function. In some embodiments, the at least one spring comprises at least one 3-D axial spring, such as those described in U.S. Pat. No. 7,887,324.

In some embodiments, at least one of the upper tray 102 and the lower tray 104 include 3-D axial springs. In some embodiments, both the upper tray 102 and the lower tray 104 include 3-D axial springs. In some embodiments, the 3-D axial springs are constructed as shown in FIGS. 6A-6C and as described below with reference to those figures. It is understood that the 3-D axial springs shown and described below with respect to FIGS. 6A-6C are provided by way of example and not by way of limitation.

FIG. 1B shows a perspective view of the oral appliance 100, which includes 3-D axial springs 126. Both the upper tray 102 and the lower tray 104 include 3-D axial springs 126.

In some embodiments, such as the embodiment shown in FIG. 6A, the 3-D axial spring 126 used in upper tray 102 and lower tray 104 of the oral appliance 100 of FIG. 1B includes an active (compression-extension) axis 154. During use, active axis 154 of the 3-D axial spring 126 is orientated at an angle approximately parallel to the long axis of the palatal/lingual surface of the tooth and/or root, instead of lying approximately parallel to the transverse axis of the palatal/lingual surface of the crown of said tooth and/or root.

In some embodiments, such as the embodiment shown in FIG. 6A, 3-D axial spring 126 includes a continuous spring body with an arm portion 150 at a proximal end 151 and a head portion 152 at a distal end 153. Arm portion 150 includes initial arm 155 that is embedded in an acrylic baseplate of upper tray 102 or lower tray 104, and a terminal arm 156 that is also embedded in the same acrylic baseplate. Both initial arm 155 and terminal arm 156 have approximately the same vertical axis: active axis 154.

In some embodiments, such as the embodiment shown in FIG. 6A, initial arm 155 and terminal arm 156 are connected by a plurality of undulating U-bends 165 that form the body or head 152 of the 3-D axial spring 126. The plurality of U-bends 165 may vary in amplitude, thereby being bigger or smaller in size relative to each other. The plurality of U-bends 165 may vary in frequency, being many or few in number. The plurality of U-bends 165 may vary in characteristic, being differently shaped, such as a 'Z' formation, a square waveform, a sinewave, a triangular wave, or any other appropriate shape that extends from side to side relative to the central axis, namely active axis 154. The plurality of U-bends 165 in the initial arm 155 and the terminal arm 156 of head portion 152 of 3-D axial spring 126 lie in close proximity with respect to each other for the entire length of active axis 154 of 3-D axial spring 126. During use, 3-D axial spring 126 lies on palatal/lingual surface of the contiguous oral structures (mucosa) orientated at an angle approximately parallel to the long axis of the palatal/lingual surface of the tooth and/or root. The head portion 152 of 3-D axial spring 126 intimately contacts the long axis of said palatal/lingual surface of said tooth.

As shown in FIG. 6B and FIG. 6C, the head portion 152 includes a first wave-shaped segment 158 (made from a plurality of U-bends 165) extending from the proximal end 151. As shown in FIG. 6C, the head portion 152 has an active axis coincident with a long axis (active axis 154) of the 3-D axial spring 126, and the head portion 152 further includes a second wave-shaped segment 162 (made from a series of U-shaped bends 165) extending from the proximal end 151 and having an axis 160 arranged about 90-degrees from the active axis 154.

In many embodiments, the 3-D axial springs 126 comprise a resilient material. Generally, the 3-D axial springs 126 may comprise a resilient material composed of any suitable material known in the art. In some embodiments, the resilient material is selected from stainless steel, Titanium-Niobium-Aluminum (Ti—Nb—Al) alloys, Cobalt-Chromium-Nickel alloys (e.g. a Cobalt-Chromium-Nickel alloy known under the trade name "Elgiloy®" available from Elgiloy Specialty Alloys of Elgin, Ill., USA), Nickel-Titanium (Ni—Ti) alloys, Ni-Ti wires that exhibits "super-elasticity", Nickel-free beta-Titanium (Ni-free β-Ti) Alloys, and combinations thereof.

In some embodiments, the 3-D axial springs 126 are formed from a wire composed of a single strand of alloy. In some embodiments, the 3-D axial springs 126 are constructed from a braided wire composed of a plurality of strands of a single alloy. In other embodiments, the 3-D axial springs 126 are constructed from a braided wire composed of a plurality of strands of a plurality of alloys.

Function of the Oral Appliance

Generally, oral appliance 100 performs at least two functions. First, oral appliance 100 enables changes to the form of the jaw and facial bones of a patient. Second, oral appliance 100 functions to provide immediate relief from disordered breathing such as sleep apnea and snoring through mandibular advancement.

In some embodiments, to treat a patient, oral appliance 100 is placed within the mouth of a patient so that overlays 137 and 144 contact at least one tooth and the remainder of the plate body 130 or 140 is spaced from the patient's tissue, including the palate. Overlays 137 and 144 prevent the patient's jaws from fully closing. Without being bound to any particular theory, it is believed that this contact of the teeth with the overlay causes intermittent forces to be applied to the body plate 130 or 140 and through the body plate 130 or 140 to the 3-D axial springs 126 and to the teeth. This cyclic intermittent signaling stimulates the patient's genome during function, essentially each time the patient speaks, swallows, chews, smiles etc., which is estimated to be about 2,000 to 3,000 times per day/night. This frequent cyclic intermittent signaling on the facial and alveolar bones is believed to cause development of the facial and jaw bones where jaw development did not fully occur during childhood. This bone development may include a descent of the palate (i.e., remodeling of the vault of the palate downwardly toward the lower jaw); a widening of the palate; an upward and outward remodeling of the body of the maxilla; and an increase in palatal length, if necessary.

In some embodiments, upper tray 102 includes a lever arm coupled to a vibrational meso-motor (not shown in the figures) capable of producing intermittent, cyclic signaling under control of a processor (not shown in the figures) to be applied to the 3-D axial springs. The motor provides intermittent cyclic signaling to at least one of the 3-D axial springs. In some embodiments, the motor provides intermittent cyclic signaling to all of the 3-D axial springs of upper tray 102. In some embodiments, the vibrational meso-motor produces ultrasonic cyclic signaling. In some embodiments, a meso-motor is incorporated into the lower tray 104 as well to provide intermittent cyclic signaling under control of a processor to the 3-D axial springs of the lower tray 104.

In some embodiments, to provide relief from disordered breathing, sleep apnea and/or snoring, oral appliance 100 includes adjustable hinge arms 110. In some embodiments, hinge arms 110 are set to a length appropriate to cause the lower jaw of the patient to be brought forward (i.e., mandibular advancement) to enlarge the airway of the patient. The patient's airway and jaw are modified as oral appliance 100 is worn. Thus, the length of adjustable hinge arms 110 will be adjusted from time-to-time so that the same beneficial effect can be maintained to improve the patients breathing when the oral appliance is worn.

In some embodiments, hinge arms 110 are removable by removing the O-rings 118 and 120 so that the oral appliance can be worn without forcing the lower jaw into a specific position with respect to the upper jaw (i.e., no mandibular advancement). This allows, for example, upper tray 102 to be worn without lower tray 104 during the day, and then, the upper tray 102 and lower tray 104 can be worn together at night to provide relief from disordered breathing through mandibular advancement by use of adjustable hinge arms 110. In some embodiments, upper tray 102 is worn without lower tray 104. In some embodiments, upper tray 102 is worn with lower tray 104.

Use Tracking

For oral appliance 100 to be effective, the patient needs to use the oral appliance 100 as instructed by the provider. To assist the provider in tracking this use, in some embodiments, appliance 100 includes a compartment (not shown) formed on a side of one of the upper tray 102 and the lower tray 104. In some embodiments, the compartment includes an opening (not shown) configured for receiving a compliance tracker (not shown). Generally, the compliance tracker measures patient treatment compliance using sensors. Generally, the compliance tracker may be selected from any suitable compliance tracker known in the art. In some embodiments, the compliance tracker is a DentiTrac compliance tracker from Braebon.

In some embodiments, the compliance tracker is configured and/or operated as described in U.S. Patent Publication 2015/0169845, which is incorporated herein by reference. In some embodiments, the compliance tracker tracks and records the use of the appliance by the patient. In some embodiments, the data recorded by the compliance tracker can be downloaded and processed using a software program run by a provider to determine the level of compliance in the patient's use of appliance 100.

Although specific embodiments have been illustrated and described herein, it will be appreciated by those of ordinary skill in the art that any arrangement, which is calculated to achieve the same purpose, may be substituted for the specific embodiment shown. This application is intended to cover any adaptations or variations of the present invention. Therefore, it is manifestly intended that this invention be limited only by the claims and the equivalents thereof.

This written description uses examples to illustrate the present disclosure, including the best mode, and also to enable any person skilled in the art to practice the disclosure, including making and using any compositions or systems and performing any incorporated methods. The patentable scope of the disclosure is defined by the claims, and may include other examples that occur to those skilled in the art. Such other examples are intended to be within the scope of the claims if they have elements that do not differ from the literal language of the claims, or if they include equivalent elements with insubstantial differences from the literal language of the claims.

As used herein, the terms "comprises," "comprising," "includes," "including," "has," "having," "contains," "containing," "characterized by" or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process or method.

The transitional phrase "consisting of" excludes any element, step, or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Where an invention or a portion thereof is defined with an open-ended term such as "comprising," it should be readily understood that (unless otherwise stated) the description should be interpreted to also describe such an invention using the terms "consisting essentially of" or "consisting of."

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As used herein, the term "about" means plus or minus 10% of the value.

What is claimed is:

1. An oral appliance comprising:
   an upper tray configured to be positioned over an upper dental arch of a patient, the upper tray including first and second posts located bilaterally on a buccal side of a posterior of the upper tray wherein the first post extends from the right-side of the upper tray and the second post extends from the left-side of the upper tray;
   a lower tray configured to be positioned over a lower dental arch of the patient, the lower tray including third and fourth posts located bilaterally on a labial side of an anterior of the lower tray wherein the third post extends from the right-side of the lower tray and the fourth post extends from the left-side of the lower tray;
   a compartment disposed on at least one of the upper tray and the lower tray, wherein the compartment comprises an opening that is configured to receive a compliance tracking recorder; and
   a first adjustable hinge arm and a second adjustable hinge arm, wherein the first adjustable hinge arm is removably coupled between the first and third posts and the second adjustable hinge arm is removably coupled between the second and fourth posts, wherein the first adjustable hinge arm and the second adjustable hinge arm are each individually configured to be held in place by O-rings and, when held in place, interlock the upper tray and the lower tray together to produce a desired amount of mandibular advancement;
   wherein the upper and lower trays are each individually coupled to at least one axial spring configured to contact a palatal/lingual surface of at least one tooth, wherein the at least one axial spring of the upper tray and the at least one axial spring of the lower tray are each individually configured to produce and transmit intermittent, cyclic forces to the palatal/lingual surface of the at least one tooth; and
   wherein the upper and lower trays each individually comprise at least two sections coupled by an expansion mechanism to enable adjustment of the size of the upper and lower trays to account for palatal expansion and upper and lower jaw development.

2. The oral appliance of claim 1, wherein the first adjustable hinge arm and the second adjustable hinge arm each individually comprise a Herbst appliance.

3. The oral appliance of claim 1, wherein the at least one axial spring of the upper tray and the at least one axial spring of the lower tray each individually comprise a 3-D axial spring comprising:
   a continuous spring body comprising an arm portion at a proximal end and a head portion at a distal end, wherein the head portion is adapted to contact the palatal/lingual surface of the at least one tooth in an orientation approximately parallel to the long axis of the tooth and anchored to one of the upper and lower trays;
   wherein the head portion comprises a first wave-shaped segment extending from the proximal end and having a first axis coincident with a long axis of the axial spring and a second wave-shaped segment extending from the proximal end and having a second axis arranged about 90-degrees from the first axis.

4. The oral appliance of claim 1, wherein the upper tray comprises a base plate comprising at least first and second parts, the base plate further comprising at least two overlays adapted to overlay an occlusal surface of posterior teeth bilaterally wherein one overlay is adapted to overlay an occlusal surface of a left-side of a jaw and the second overlay is adapted to overlay a second occlusal surface of a right-side of the jaw.

5. The oral appliance of claim 4, wherein the first half and the second half each further comprise a hard acrylic material.

6. The oral appliance of claim 4, wherein the expansion mechanism further comprises: an expansion jackscrew disposed intermediate to, and coupling, the first part of the base plate to the second part of the base plate.

7. The oral appliance of claim 1, wherein the at least one axial spring of the upper tray and the at least one axial spring of the lower tray each individually comprise a braided wire composed of a plurality of strands of alloy.

8. The oral appliance of claim 1, wherein the at least one axial spring of the upper tray and the at least one axial spring of the lower tray are each individually configured to produce intermittent, cyclic forces to the palatal/lingual surface of the tooth by intermittent contact of opposing teeth in the maxillary and mandibular dental arches, during swallowing, speech, and/or mastication.

9. The oral appliance of claim 1, wherein the expansion mechanism is made of a self-expanding material.

10. The oral appliance of claim 1, wherein the at least one axial spring of the upper tray and the at least one axial spring of the lower tray each individually comprise a wire composed of a single strand of alloy.

11. The oral appliance of claim 1, wherein at least one of the at least one axial spring of the upper tray and the at least one axial spring of the lower tray further comprises a lever arm coupled to a vibrational meso-motor capable of producing intermittent, cyclic signaling.

12. The oral appliance of claim 11, wherein the vibrational meso-motor produces ultrasonic cyclic signaling.

13. An oral appliance comprising:
   an upper tray configured to be positioned over an upper dental arch of a patient, the upper tray including first and second posts located bilaterally on a buccal side of a posterior of the upper tray wherein the first post extends from the right-side of the upper tray and the second post extends from the left-side of the upper tray; and
   a compartment disposed on the upper tray, wherein the compartment comprises an opening that is configured to receive a compliance tracking recorder;
   wherein the first post is configured to receive a first adjustable hinge arm and the second post is configured to receive a second adjustable hinge arm, wherein the first and second adjustable hinge arms are non-permanently attached to the first and second posts, respectively, with O-rings;
   wherein the upper tray comprises at least one axial spring configured to contact a palatal/lingual surface of at least one tooth, wherein the at least one axial spring is coupled to the upper tray, wherein the at least one axial spring is configured to produce and transmit intermittent, cyclic forces to the palatal/lingual surface of the tooth; and
   wherein the upper tray comprises at least two sections coupled by an expansion mechanism to enable adjustment of the size of the upper tray to account for palatal expansion and upper jaw development.

14. The oral appliance of claim 13, wherein the at least one axial spring of the upper tray and the at least one axial spring of the lower tray each individually comprise a wire composed of a single strand of alloy.

15. The oral appliance of claim 13, wherein the first adjustable hinge arm and the second adjustable hinge arm each individually comprise a Herbst appliance.

16. The oral appliance of claim 13, wherein the at least one axial spring of the upper tray and the at least one axial spring of the lower tray each individually comprise a 3-D axial spring comprising:
 a continuous spring body comprising an arm portion at a proximal end and a head portion at a distal end, wherein the head portion is adapted to contact the palatal/lingual surface of the at least one tooth in an orientation approximately parallel to the long axis of the tooth and anchored to one of the upper and lower trays;
 wherein the head portion comprises a first wave-shaped segment extending from the proximal end and having a first axis coincident with a long axis of the axial spring and a second wave-shaped segment extending from the proximal end and having a second axis arranged about 90-degrees from the first axis.

17. The oral appliance of claim 14, wherein the upper tray comprises a base plate comprising at least first and second parts, the base plate further comprising at least two overlays adapted to overlay an occlusal surface of posterior teeth bilaterally wherein one overlay is adapted to overlay a first occlusal surface of a left-side of a jaw and the second overlay is adapted to overlay a second occlusal surface of a right-side of the jaw.

18. The oral appliance of claim 17, wherein the first part and the second part each individually further comprise a hard acrylic material.

19. The oral appliance of claim 17, wherein the expansion mechanism further comprises: an expansion jackscrew being disposed intermediate to, and coupling, the first part of the base plate to the second part of the base plate.

20. The oral appliance of claim 13, wherein the at least one axial spring of the upper tray and the at least one axial spring of the lower tray each individually comprise a braided wire composed of a plurality of strands of alloy.

21. The oral appliance of claim 13, wherein the at least one axial spring of the upper tray and the at least one axial spring of the lower tray are each individually configured to produce intermittent, cyclic forces to the palatal/lingual surface of the tooth by intermittent contact of opposing teeth in the maxillary and mandibular dental arches, during swallowing, speech, and/or mastication.

22. The oral appliance of claim 13, wherein the expansion mechanism is made of a self-expanding material.

* * * * *

UNITED STATES PATENT AND TRADEMARK OFFICE
CERTIFICATE OF CORRECTION

| | |
|---|---|
| PATENT NO. | : 11,723,790 B2 |
| APPLICATION NO. | : 17/522769 |
| DATED | : August 15, 2023 |
| INVENTOR(S) | : Singh et al. |

It is certified that error appears in the above-identified patent and that said Letters Patent is hereby corrected as shown below:

On the Title Page

Item (12) delete "Huntsman et al." and insert -- Singh et al. --

Item (72) should read:
Inventors: Gurdev Dave Singh, Raleigh, NC (US); Todd Nickolas Huntsman, Flower Mound, TX (US); Braden Charles Bennett, Provo, UT (US); Justin Dean Harris, Lehi, UT (US); Cathryn H. Bonar, Owensboro, KY (US)

Signed and Sealed this
Seventh Day of May, 2024

Katherine Kelly Vidal
*Director of the United States Patent and Trademark Office*